(12) United States Patent
Zhang et al.

(10) Patent No.: US 10,330,612 B2
(45) Date of Patent: Jun. 25, 2019

(54) MULTI-FUNCTION X-RAY METROLOGY TOOL FOR PRODUCTION INSPECTION/MONITORING OF THIN FILMS AND MULTIDIMENSIONAL STRUCTURES

(71) Applicant: Applied Materials, Inc., Santa Clara, CA (US)

(72) Inventors: Lin Zhang, San Jose, CA (US); Shuran Sheng, Saratoga, CA (US); Andrew V. Le, Santa Clara, CA (US)

(73) Assignee: Applied Materials, Inc., Santa Clara, CA (US)

( * ) Notice: Subject to any disclaimer, the term of this patent is extended or adjusted under 35 U.S.C. 154(b) by 521 days.

(21) Appl. No.: 14/521,345

(22) Filed: Oct. 22, 2014

(65) Prior Publication Data
US 2016/0077025 A1 Mar. 17, 2016

Related U.S. Application Data (60) Provisional application No. 62/049,253, filed on Sep. 11, 2014.

(51) Int. Cl.
*G01N 23/00* (2006.01)
*G01N 23/201* (2018.01)
*G01T 7/08* (2006.01)
*G01N 23/207* (2018.01)
*G03F 7/20* (2006.01)
*H01L 21/66* (2006.01)

(52) U.S. Cl.
CPC ......... *G01N 23/201* (2013.01); *G01N 23/207* (2013.01); *G01T 7/08* (2013.01); *G03F 7/70625* (2013.01); *G01N 2223/071* (2013.01); *G01N 2223/602* (2013.01); *H01L 22/12* (2013.01)

(58) Field of Classification Search
CPC ............... G01N 23/201; G01N 23/207; G01N 2223/071
See application file for complete search history.

(56) References Cited

U.S. PATENT DOCUMENTS

2006/0062351 A1* 3/2006 Yokhin ............ G01N 23/20008
378/86
2008/0273662 A1* 11/2008 Yun ....................... G01N 23/201
378/74
2016/0223706 A1 8/2016 Franco et al.

* cited by examiner

*Primary Examiner* — Dani Fox
(74) *Attorney, Agent, or Firm* — Patterson + Sheridan, LLP (57) ABSTRACT

An apparatus for integrating metrology and method for using the same are disclosed. The apparatus includes a multi-chamber system having a transfer chamber, a deposition chamber, an etch chamber and a metrology chamber, and a robot configured to transfer a substrate between the deposition chamber or etch chamber and the metrology chamber.

20 Claims, 7 Drawing Sheets

FIG. 7B

MULTI-FUNCTION X-RAY METROLOGY TOOL FOR PRODUCTION INSPECTION/MONITORING OF THIN FILMS AND MULTIDIMENSIONAL STRUCTURES

CROSS-REFERENCE TO RELATED APPLICATIONS

This application claims benefit of U.S. Provisional Application Ser. No. 62/049,253, filed Sep. 11, 2014, of which is incorporated by reference in s entirety.

BACKGROUND

Field

Embodiments of the invention relate to a method and apparatus for inspecting thin films and multidimensional structures. More particularly, the disclosures relate to a method and apparatus for integrating metrology tools in a multi-chamber vacuum processing system and the like.

Background of the Related Art

The fabrication of microelectronics devices typically involves a complicated process sequence requiring hundreds of individual steps performed on semiconductive, dielectric and conductive substrates. Examples of these process steps include oxidation, diffusion, ion implantation, thin film deposition, cleaning, etching and lithography. As one of leading technologies, NAND scaling is driving fast transition from planar 2D to 3D devices. However, the 3D NAND technology is now encountering new challenges, such as process control, inspection and metrology. Among others, gate stack integrity is as critical as wafer quality. The immediate challenge is how to effectively and accurately measure the thickness (& critical dimensions), roughness, stress, density and defects of complex stacks & structures, such as gate multilayer complex oxide-nitride-oxide (ONO) or oxide-poly-oxide (OPO) stacks of up to a few hundred pairs.

With ever-decreasing device dimensions, the control of critical dimensions and process uniformity becomes increasingly more important. Complex multilayer stacks require precise process monitoring the critical dimensions for the thickness, roughness, stress, density, and potential defects. The critical dimensions are verified by measuring the dimensions with a metrology tool. Conventional tools using transmission electron microscopes (TEM) or scanning electron microscopes (SEM) imaging utilize destructive testing techniques, and are costly and time-consuming, making the conventional tools incapable of automation or in-line integration. Current non-destructive metrology tools in production fabs, including broadband spectroscopic ellipsometry technology, can measure only total thickness of multilayer stacks and cannot measure optically opaque thick metallic films, which have been extensively used for semiconductor device fabrication.

Therefore, there is an ongoing need for improved metrology tools.

SUMMARY

In one embodiment a metrology has a transmitting module with an x-ray generator and an optic configured for transmitting an incident ray, a receiving module with an optic for collecting the incident ray and directing the incident ray to a sensor, and a software module attached to the metrology tool operable to control the transmitting module and the receiving module, wherein the software module is configured to collect and process data from the sensor.

In another embodiment, a multi-chamber system has a vacuum-tight processing platform and a factory interface. The vacuum-tight processing platform has a plurality of processing chambers configured to operate below atmospheric pressure, where the plurality of processing chambers may include a transfer chamber having a robot configured to transport a substrate, a chemical vapor deposition chamber, an etch chamber, and a load lock chamber. The factory interface has a robot configured to transport the substrate. A metrology, in communication with the multi-chamber system, has a transmitting module with an x-ray generator and an optic configured for transmitting an incident ray, a receiving module with an optic for collecting the incident ray and directing the incident ray to a sensor, and a software module attached to the metrology tool operable to control the transmitting module and the receiving module, wherein the software module is configured to collect and process data from the sensor.

In yet another embodiment, a method for processing a substrate is provided. A metrology tool is provided and operatively coupled to a chamber of a multi-chamber system. The substrate is processed in the chamber of the multi-chamber system. One or more x-ray measurements are performed by the metrology tool in the processing chamber and a substrate characteristic is determined from the x-ray measurements.

BRIEF DESCRIPTION OF THE DRAWINGS

A more particular description of the invention, briefly summarized above, may be had by reference to the embodiments thereof which are illustrated in the appended drawings. It is to be noted, however, that the appended drawings illustrate only typical embodiments of this invention and are therefore not to be considered limiting of its scope, for the invention may admit to other equally effective embodiments.

To facilitate understanding, identical reference numerals have been used, wherever possible, to designate identical elements that are common to the figures. It is also contemplated that elements of one embodiment may be advantageously incorporated in other embodiments without further recitation.

DETAILED DESCRIPTION

Figure 1:
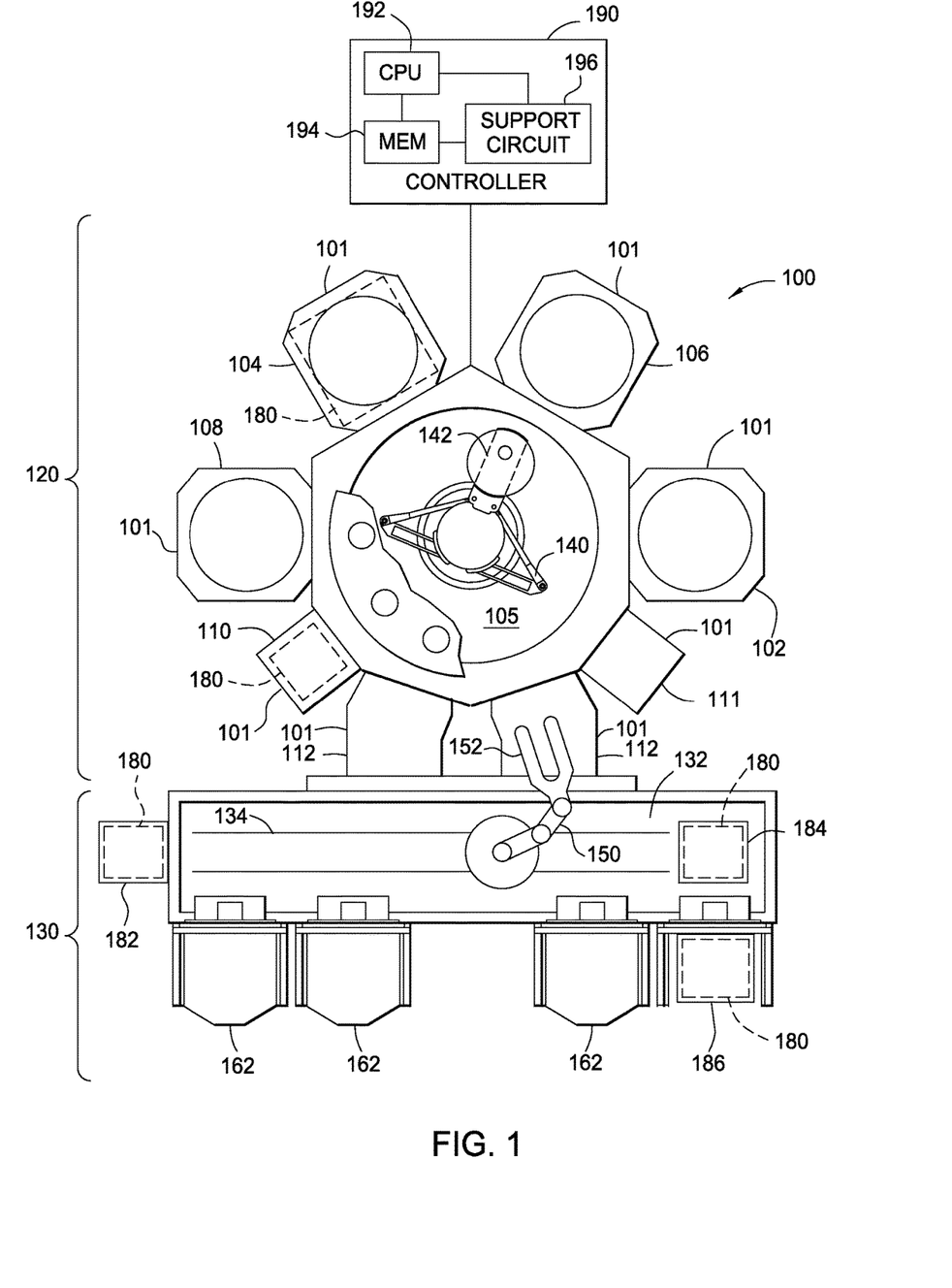
FIG. 1 is a schematic diagram showing a multi-chamber vacuum processing system having an integrated metrology chamber.

Embodiments of the present disclosure relate to a method and apparatus for a metrology tool which may stand alone or be integrated with a multi-chamber vacuum processing system, such as an in-line or cluster vacuum processing tool. By providing non-destructive metrology capabilities during processing, the process monitoring and process control can be greatly facilitated. FIG. 1 is a schematic diagram showing a top view of a multi-chamber vacuum processing system 100 having an integrated non-destructive metrology tool 180. The multi-chamber vacuum processing system 100 also includes a system controller 190, a vacuum-tight processing platform 120 and a factory interface 130.

The vacuum-tight processing platform 120 has a plurality of attached chambers 101 disposed around a transfer chamber 105. The transfer chamber 105 is coupled to a vacuum system (not shown) for providing a reduced atmosphere condition in the vacuum-tight processing platform 120. The transfer chamber 105 houses a robot 140. The robot 140 has a retractable blade 142 configured to support a substrate. The robot 140 has a range of motion operable to transfer substrates disposed on the retractable blade 142 to and from the attached chambers 101.

One of the attached chambers 101, such as chamber 112, may be a load lock chamber. Another one of the attached chambers 101, such as process chamber 108, may be an etch chamber. Some of the attached chambers 101 may be a deposition chambers. The deposition chambers may include one of a chemical vapor deposition 102, a physical vapor deposition chamber 106, and an atomic layer deposition chamber 104. Additionally, one of the attached chambers 101, such as process chamber 110 or process chamber 111, may be a metrology chamber, orientation chamber, de-gas chamber or other suitable chamber.

The process chamber 110, when configures as a metrology chamber, is operatively coupled to the metrology tool 180. The metrology tool 180 which performs measurements on a substrate disposed inside the process chamber 110. The metrology tool 180 may be a multi-function X-ray metrology tool used to perform measurements on a substrate that has been, or is to be, processed in one or more of the process chambers 101, as shown as phantom in chamber 104. Information regarding substrate characteristics can be extracted from the measurements obtained by the metrology tool 180, and decisions can be made as to whether additional processing may be needed for that substrate, or whether the process conditions in the process chamber 108 should be adjusted.

The factory interface (FI) 130 may have a plurality of front opening universal pods (FOUPs) 162 and a FI robot 150. The FI 130 may also have a chamber or station suitable for housing the metrology tool 180. For example, the metrology tool 180 may be located at a station 182 attached to an end of the FI 130, a station 184 disposed on an interior surface 132 of the FI 130, or a station 186 in place of one of the FOUPs 162.

The FI robot 150 may have rails 134 and a moveable blade 152. The FI robot 150 is configured to have a range of motion sufficient to transfer substrates the moveable blade 152 between the FOUPs 162, the metrology tool 180 if present in the FI 130, and the load lock chambers.

The system controller 190 is coupled to and controls each chamber or module of the multi-chamber vacuum processing system 100. Generally, the system controller 190 may control all aspects of operation of the processing system 100 using a direct control of chambers and apparatus of the processing system 100 or, alternatively, by controlling the computers associated with these chambers and apparatus. Furthermore, the system controller 190 may also be configured to communicate with a control unit associated with the metrology tool 180. For example, movements of the robot 140, transferring substrates to and from the process chambers 102, 104 and 106 and the metrology chamber 110, performing process sequences, coordinating operations of the metrology tool 180 with various components of the multi-chamber vacuum processing system 100, and so on, may be controlled by the system controller 190.

In operation, the system controller 190 enables feedback from the respective chambers and apparatus to optimize substrate throughput. The system controller 190 comprises a central processing unit (CPU) 192, a memory 194, and a support circuit 196. The CPU 192 may be one of any form of a general purpose computer processor that can be used in an industrial setting. The support circuit 196 is conventionally coupled to the CPU 192 and may comprise cache, clock circuits, input/output subsystems, power supplies, and the like. The software routines, when executed by the CPU 192, transform the CPU into a specific purpose computer (controller) 190. The software routines may also be stored and/or executed by a second controller (not shown) that is located remotely from the multi-chamber vacuum processing system 100, such as at the metrology tool 180.

Although the metrology tool 180 is discussed in relation to the process chambers 101 throughout this discussion, the metrology tool 180 may be integrated with other chambers 101 or the FI 130. For example, the metrology tool 180 may work to provide in-situ measurements integrated with process monitoring and control in the process chambers 101, e.g., the chemical vapor deposition 102 used to deposit material on the substrate or the etch chamber 108 used for etching. Additionally, the metrology tool 180 may be provided as a standalone system unattached and remote from the processing system 100, but communicating with the system 100 to provide information utilized for process monitoring and control within the chambers 101 or elsewhere within the system 100.

Figure 2:
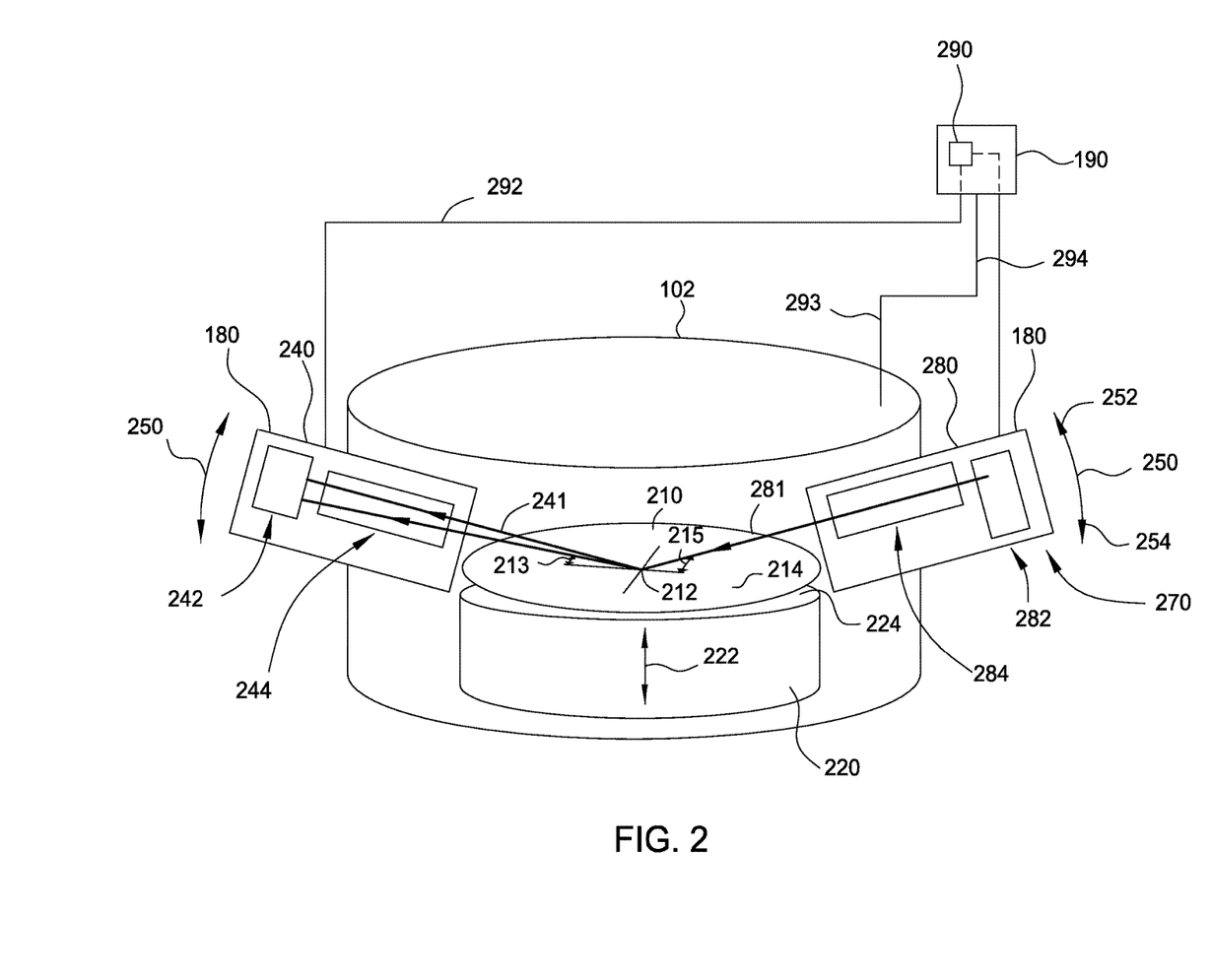
FIG. 2 is a schematic for a metrology tool suitable for use in-situ in the multi-chamber vacuum processing system.

FIG. 2 is a schematic for the metrology tool 180 suitable for in-situ use in the multi-chamber vacuum processing system 100. The metrology tool 180 has a software module 290, a transmitting module 280 and a receiving module 240. The transmitting module 280 and the receiving module 240 may be associated with one or more of the processing chambers 101, such as the chemical vapor deposition (CVD) chamber 102 in FIG. 1. The following discussion of FIG. 2 is provided with respect to the metrology tool 180 configured to measure a substrate 210 in-situ while the substrate 210 is undergoing processing in the CVD chamber 102. However, it should be appreciated that the metrology tool may be located in any chamber 101 of the vacuum-tight processing platform 120 and/or in the factory interface 130 of the processing system 100, as well as a standalone system, as will be discussed in FIG. 3.

The CVD chamber 102 has a substrate support 220. The substrate support 220 has a top surface 214 configured to support the substrate 210 thereon. The substrate support 220 may be configured to move in a vertical direction as shown by arrow 222. The CVD chamber 102 may be controlled by the system controller 190 through an input/output connection 293. The system controller 190 may provide instructions for the substrate support 220 to move up or down in the vertical direction as well as instructing the CVD chamber 102 on processes performed therein.

The metrology tool 180 has a multi-function X-ray for measuring the parameters for various CD on the substrate 210 for production inspection/monitoring of complex stacks & structures. The metrology tool 180 may also include three function modules: the x-ray metrology module 270, the software module 290 and the front end module for controlling automation integration (substrate load/unload, etc.).

The X-ray metrology module 270, may use both primary and complementary techniques for obtaining CD measurement data. The primary techniques may include one of small-angle X-ray diffraction (SAXRD) and small-angle X-ray scattering (SAXS). The small angle x-ray diffraction (SAXRD) and small angle x-ray scattering (SAXS) techniques can be applied to inspect in-line or off-line substrates.

In one embodiment, the metrology tool 180 uses SAXRD's capability of measuring one dimension (1D) periodic multilayers for process monitoring in device manufacturing. The SAXRD technique may measure the modulation periods for periodic multilayers (such as ONO, OPO stacks) or "super-lattices", i.e., a periodic structure of layers of two (or more) materials, which may range from about 1 nm to about 100 nm. The SAXRD technique may measure individual layer thickness for $SiO_2$ and $Si_3N_4$ in ONO, and $SiO_2$ and poly-Si in OPO. The SAXRD technique measures the diffraction peaks from these synthetic nanostructures at very low angles, such as less than about 3 degrees. SAXRD technique can measure a wide variety of materials, ultrathin (~10 nm) to very thick (several to tens of microns), crystalline or amorphous, semiconductor, metal, dielectric, magnetic or organic. The SAXRD technique detects individual layer's thickness' drift and film/interface roughness and density. Thus, SAXRD may be used to determine how much the top or bottom layer is drifting from each other and the overall process.

The metrology tool 180 may use SAXS for inspecting 3D nano-structures (or 3D "super-lattices") for devices formed after ONO or OPO stack depositions. SAXS is related to the shape and size of nanostructures and the distances of ordered features, i.e., the distance between individual nanostructures. The measurable sizes or dimensions range from about less than 1 nm to about 25 nm, and up to about 200 nm for repeating structures. The SAXS is capable of measuring along all three axis to determine the CD of 3D NAND nanostructures. This makes SAXS well suitable to inspect 3D NAND nanostructures. The SAXS techniques may be used for post etch inspection for detecting the via size, via spacing distribution, via fill with poly-Si, post trench open inspection, and post W-gate electrode deposition inspection. The SAXS technique may also be used to inspect 3D nano-structures (3D "supper lattice"), comprised of various materials, such as metallic, dielectric, magnetic, crystalline, amorphous, optically opaque, organics and/or liquids.

The secondary techniques include at least one or more of grazing incidence X-ray diffraction (GI-XRD), X-ray reflectivity (XRR), and high resolution X-ray diffraction (HR-XRD). The X-ray metrology module 270 is capable of switching between the primary and the secondary techniques to select the technique best suited for measured results.

The secondary techniques are complimentary to the primary techniques and provide for a broad variety of testing and monitoring. For example GI-XRD, XRR, HR-XRD may be useful for single-crystal & epitaxial layer structures to investigate crystallinity, strain/stress, thickness, composition and density. Additionally, XRF, GI-XRF provides information for determining composition, metal contamination, and defect inspection/analysis. The XRD techniques provide information indicative of crystallography, phase, strain/stress, and texture analysis. In some embodiments, these complimentary techniques are formed using the same X-ray source, the sample stage with SAXRD/SAXS, combined with additional optics and detector sets (or sub-modules, one for each technique), and with additional software functions. This could add techniques selected by users with reasonable costs to the basic tool with the primary techniques.

The software module 290 of the metrology tool 180 may be provided for controlling the operation of the metrology tool 180, e.g., implementing metrology measurements, acquiring and storing data, analyzing results, and so on. This software module 290 may be configured to communicate with the system controller 190 for allowing various operations to be performed in a coordinated fashion. In one embodiment, the software module 290 is integrated into the system controller 190. Alternately, the software module 290 may be configured as a standalone terminal or other suitable device for controlling the metrology tool 180 and storing or transmitting data captured by the metrology tool 180.

Figure 5:
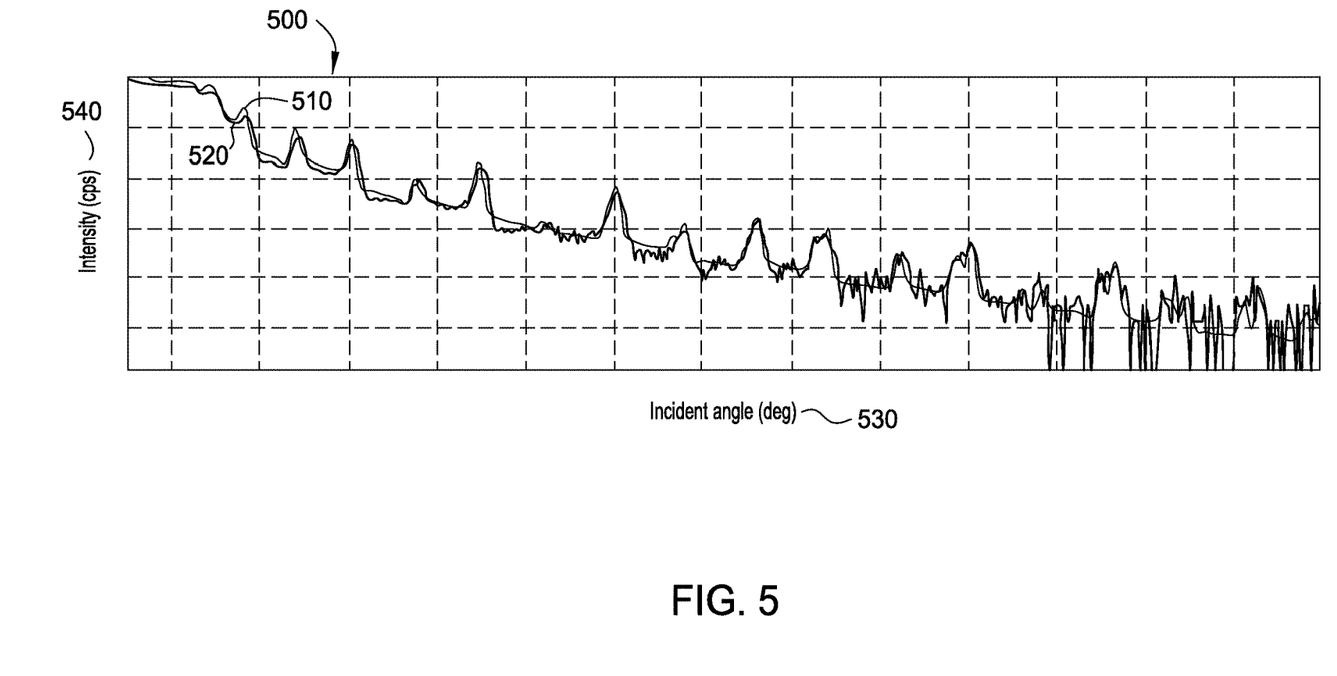
FIGS. 5, 6 and 7A through 7D are results for an X-ray intensity plotted against an incident angle for the X-ray.
Figure 6:
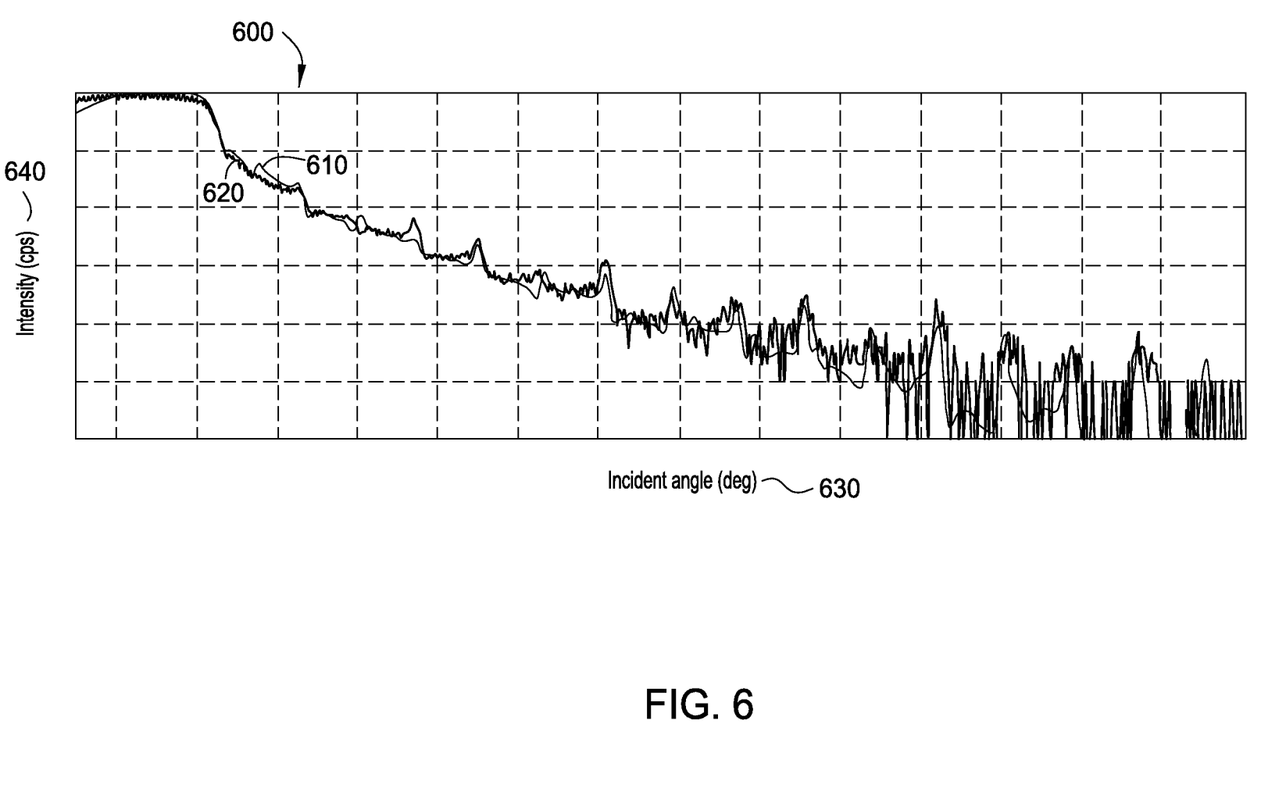

The software module 290 may include sub-modules. A first sub-module is an X-ray metrology data acquisition, analysis (simulation) and reporting (DAR) module. The DAR module introduces a new physical model for SAXRD data analysis/simulation to enable accurate 1D periodic multilayer measurement for device manufacturing. FIGS. 5, 6 and 7 show the results for an X-ray intensity plotted against an incident angle for the X-ray. For a 72× pair ON stack and a 38× pair OP stack, the new physical model further extends the SAXRD's capabilities to perform spatially resolved measurements for both the ONO and OPO stacks. The model uses a multi-segmented stack structure to allow for parameter (thickness, roughness, density) variations of the layers from different segments. The model enables the SAXRD to detect if any layer parameter drifts. $SiO_2$ layers are more prone to drift thinner as growth is continued for both the ONO and OPO processes. The poly-Si layers drift thinner to a lesser degree than the SiN layers, while the SiN layer growth is relatively stable. The results obtained using SAXRD are very close to those obtained by TEM imaging, confirming high accuracy and precision of the SAXRD metrology.

FIG. 5 illustrates a plot 500 of intensity 540, in counts per second (CPS), along a Y axis, against an incident angle 530, in degrees, along an x axis for an ONO stack. The plot 500 compares an SAXRD model 510 and raw data 520. The SAXRD model 510 demonstrates a good fit with the raw data 520 even with multi segmented ONO stacks and varying thickness. Accuracy and precision was confirmed by TEM which measured pair thickness drift of about 2.4% compared to the SAXRD modeled thickness drift of about 2.1%.

FIG. 6 illustrates a plot 600 intensity 640, in counts per second (CPS), along a Y axis, against an incident angle 630, in degrees, along an x axis for an OPO stack. The plot 600 compares an SAXRD model 610 and raw data 620 for a 38 pair OPO stack.

Figure 7A:
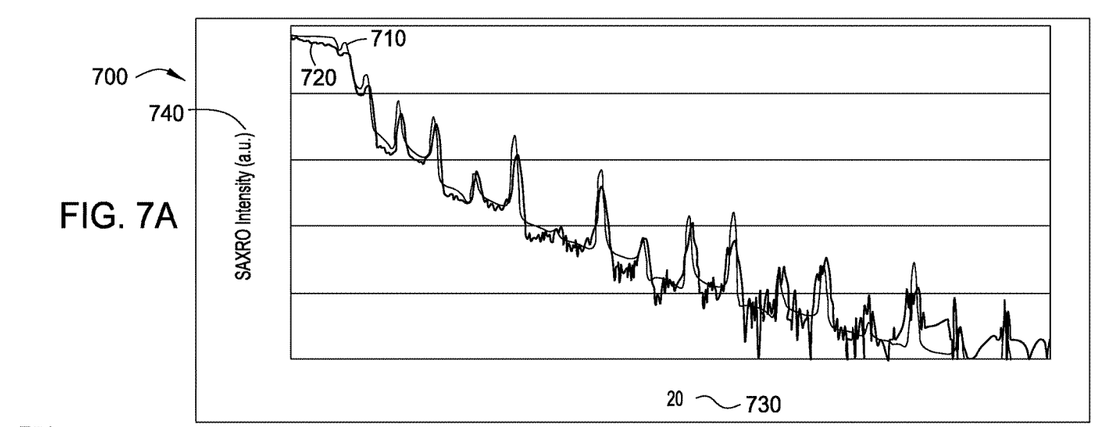
Figure 7B:
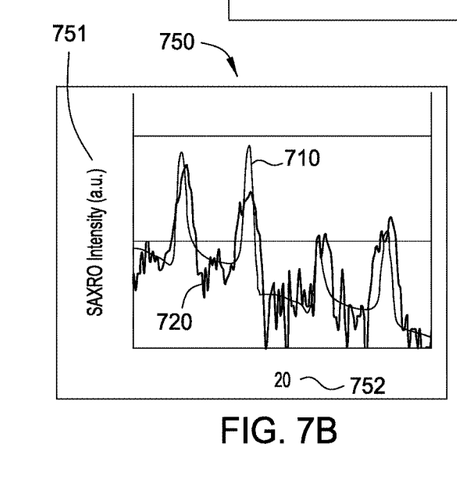
Figure 7C:
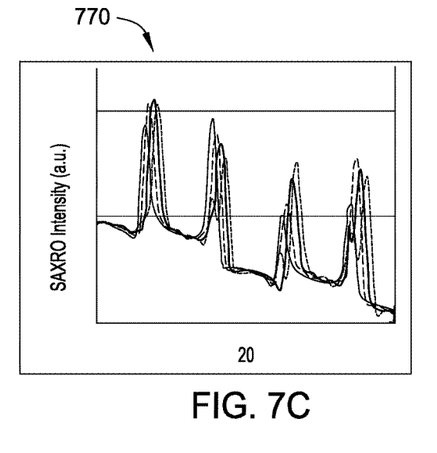
Figure 7D:
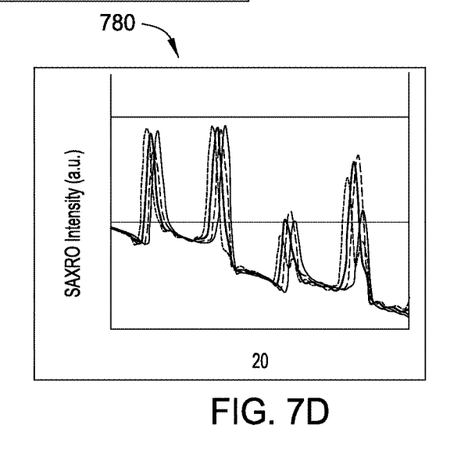

Further simulation by slightly varying SiO2 layer thickness shows that SAXRD is able to readily detect <1 nm variations in layer thickness, which quickly allows detection of process drift or information on how the process is drifting. FIGS. 7A through 7D show SAXRD sensitivity to less than 1 nm layer thickness variations. In FIG. 7A, a graph 700 of the intensity 740 versus twice the angle of incidence 730 for a 72 pair ONO layer is shown for raw data plot 720 and model simulated plot 710. FIG. 7B is a partial view of the graph 700 for the model simulated plot 710 to use for further comparison with FIGS. 7C and 7D. The raw data plot 720 is shown for reference only in FIG. 7B. FIG. 7C depicts the partial view of the graph 700 shown in FIG. 7B for the model simulated plot 710 along with the same model but with thickness a negative variation of 1, 2 and 3%. FIG. 7D depicts the partial view of the graph 700 shown in FIG. 7B for the model simulated plot 710 along with the same model but with thickness a positive variation of 1, 2 and 3%. As can be seen in FIGS. 7C and 7D, layer thickness drift of less than 1 nm can be easily identified. The process drift may be monitored and measured in-situ by the metrology tool 180 and provide feedback to the system controller 190 for making adjustments in the chamber or processing recipe to correct the process drift. Similar methodology may be used to develop new models for the SAXS to enable 3D NAND nano-structure inspection as well as other 3D nano-structure inspection.

The second sub module of the software module 290 is a control module. The control module provides automation and control of hardware functions, such as control of the transmitting module 280 and receiving module 240. For example, the control module may provide mechanical/optical alignment of the transmitting module 280 and receiving module 240. The control module positions the transmitting module 280 and receiving module 240 for scanning and mapping the substrate 210 surface. The software module is able to switch quickly between the sub-modules.

The transmitting module 280 has an x-ray source 282, i.e. x-ray generator tube, and x-ray optics 284. The x-ray source 282 generates an incident ray 281 that strikes a top surface 214 of the substrate 210. The angle between the incident ray 281 and the top surface 214 is the incidence angle 216. The incidence angle 216 may be adjusted with the rotation of the transmitting module 280 in a counterclockwise 252 or clockwise 254 manner as shown by arrow 250. For example, rotating the transmitting module 280 clockwise 254 minimizes the incidence angle 216. The transmitting module 280 may be rotated such that the incidence angle 216 may be between about 0.5 degrees and about 6 degrees, such as about 1.5 degrees.

The software module 290 may control the x-ray optics 284 to adjust the incident angle 216 for the incident ray 281. The larger the incident angle 216, the deeper the penetration of the X-ray into the substrate 210 for measuring structures therein. For example in silicon, a small incident angle 216, such as about 0.5 degrees may be useful for measuring structures which are about 1 um. A medium incident angle 216, such as about 3 degrees may be useful for measuring structures which are about 10 um. A large incident angle 216, such as about 6.0 degrees may be useful for measuring structures which are about 20 um or greater. Thus, a vertical profile may be accurately obtained for the structure by adjusting the incident angle accordingly.

The receiving module 240 has an x-ray optics 244 and a detector 242. The x-ray optics 244 collects the diffracted, scattered and fluoresced rays 241. The rays 241 may propagate from the top surface 214 of the substrate 210 at a diffracted angle 213. The diffracted angle 213 may be the same or different than the incident angle 216.

The x-ray optics 284, 244 may be configured for one or more x-ray metrology methods. For example, the x-ray optics 284, 244 may be configured for SA-XRD, SAXS, among other techniques. The metrology tool 180 may use the same x-ray source 282 and different x-ray optics 284, 244 to switch between one technique to another, such as switching between SA-XRD and SAXS. The internal optics of the x-ray optics 244 may have optional optics which may be switched, replaced, rotated automatically or moved to operate with SA-XRD, SAXS or other suitable techniques for measuring 3D NAND features. Additionally, the x-ray source 282 may include one or more mechanisms for providing different x-ray sources suitable for switching between SA-XRD, SAXS, among other techniques.

The metrology tool 180 may measure substrate CD in-situ in the CVD chamber 102. The transmitting module 280 is configured to generate the incident ray 281 at the incident angle 216 for measuring a spot 212 on the top surface 214 of the substrate. The spot 212 may be about 10 nm to about 20 mm depending on the techniques utilized by the transmitting module 280. For example, the size of the spot 212 may be about 10 um to about 100 um in size for SA-XRD or SAXS. The diffracted rays 241 leave the spot 212 at the diffracted angle 213 and are collected by the receiving module 240. The software module 290 may collect the data from the receiving module 240 and use the collected data to determine the characteristics of the substrate at the location of the spot 212.

The metrology tool 180 is well suited for in-situ measurement as it uses non-destructive X-ray metrology which is capable of probing to the nanoscale level and characterizes various materials, i.e, powders, thin films and bulk materials, crystalline and amorphous, optically opaque, organic or liquid samples, without calibration curves, or reference samples. The sampling depth may be greater that about 2 nm. For example, the X-ray sampling depth can range from about 2 nm to about 10 nm and is extendable to about 30 um. The metrology tool 180 may probe rough (greater than about 2 nm) or discontinuous interfaces/surfaces and at angles above about 0.1 degrees to about 0.5 degrees even at depths exceeding 1 um.

Thus, the hardware design of the transmitting module 280 and receiving module 240 coupled with the software module 290 can enable the full automated control of X-ray source, optics, detector, goniometer, sample stage (wafer loading, mapping, etc) and fast switching between the sub-modules required for each technique, for production fabrication applications.

A complete in-situ scan for the top surface 214 of the substrate 210 in the CVD chamber 102 may be accomplished with an articulating substrate support, a robot blade, or moving the transmitting module 280 and the receiving module 240 in a manner to direct the incident ray 281 at a plurality of locations along the top surface 214 of the substrate 210. A chamber 101 may be specifically configured to provide these capacities. Alternately, the metrology tool may be a standalone tool or attached to the factory interface 130.

Figure 3:
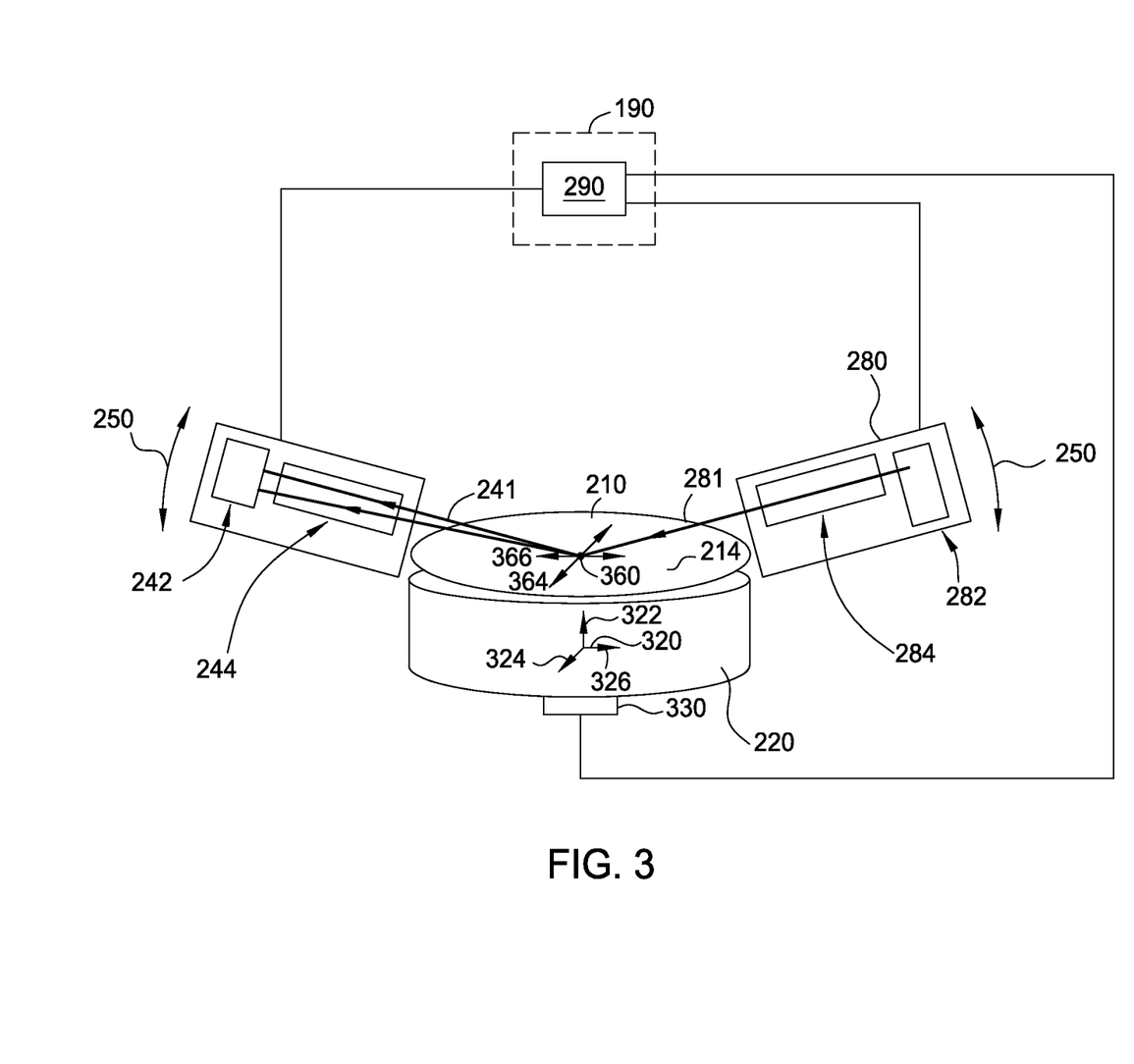
FIG. 3 is a schematic for a standalone metrology tool suitable for use with the multi-chamber vacuum processing system.

FIG. 3 is a schematic for a standalone metrology tool suitable for use with the multi-chamber vacuum processing system. The stand alone metrology tool may have an actuator 330 for articulating the substrate support 220. The actuator 330 may provide movement in an X-direction 326, a Y-direction 324, and a Z-direction 322. For example, the actuator 330 may be configured to move the substrate support 220 up to about 450 mm in the X-direction 326 and the Y-direction 324. A spot 360 on the top surface 214 of a substrate 210 where the transmitting module 280 directs the incident ray 281 for measuring the substrate, may be made to move along a coordinate in a X 366 plane or Y 364 plane without moving the transmitting module 280. Alternately, or additionally, the actuator 330 may rotate about the plane of the X-direction 326 and Y-direction 324. In this manner, the actuator 330 may only have to provide movement in a single direction, such as the X-direction 326, and entirely across the top surface 214 of the substrate 210 by rotating the substrate support 220.

Figure 4:
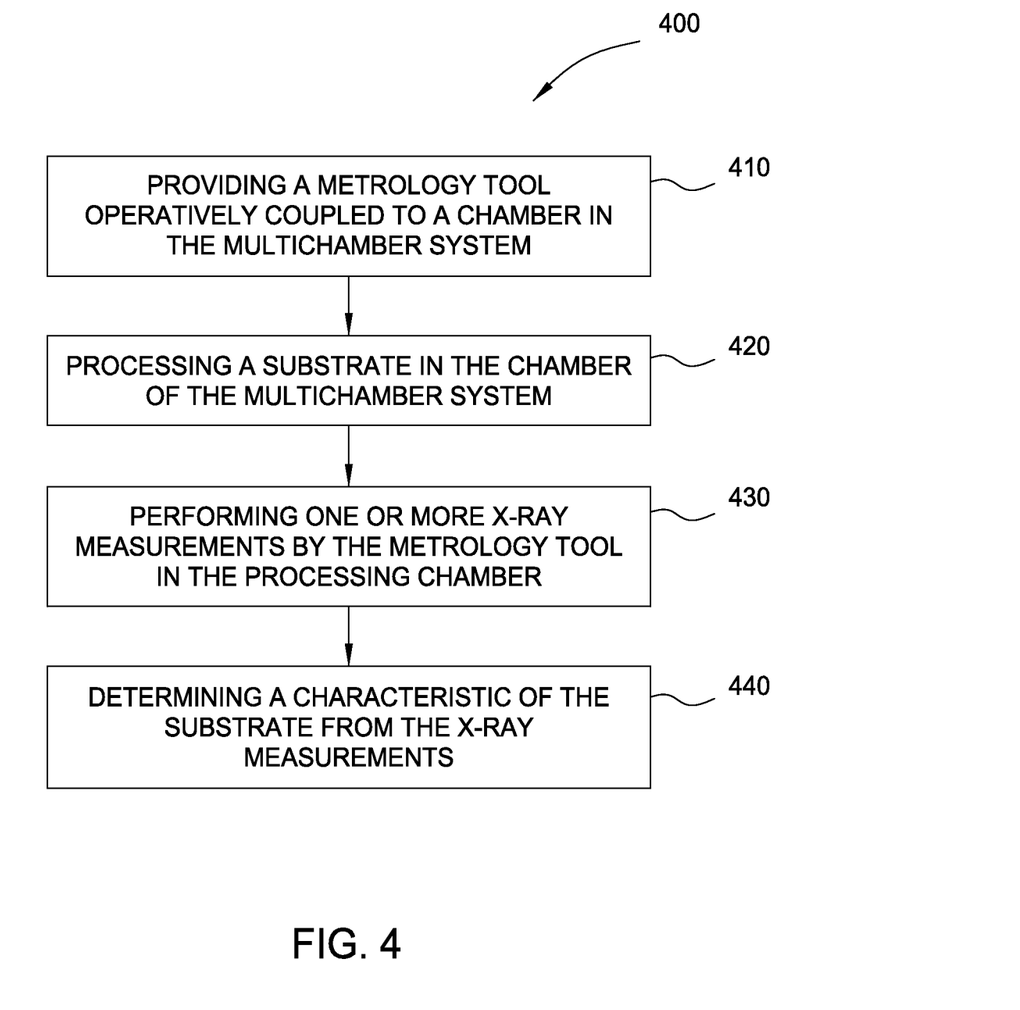
FIG. 4 is a method for production inspection of a multidimensional structure.

FIG. 4 is a method 400 for production inspection of a multidimensional structure. FIG. 4 illustrates the sequence that can be implemented using the apparatus of the present invention. A suitable system, such as the multi-chamber system comprising a transfer chamber and a processing chamber, may be provided for discussing the method 400. In block 410, a metrology tool is operatively coupled to the processing chamber in the multi-chamber system. Alternately, the metrology tool is coupled to a factory interface portion of the multi chamber system or provided as a standalone apparatus. A substrate is processed in the processing chamber at block 420. X-ray measurements of the substrate are performed in the processing chamber at block 430. The measurements may be performed in-situ to reduce substrate transfer steps. Alternately, the substrate is transferred to a second processing chamber, the factory interface or a standalone system for performing the x-ray measurements with the metrology tool. In block 440, a substrate characteristic is determined from the at least one x-ray measurement. Depending on the specific processing needs, additional method steps or variations may be implemented for process monitoring or control using the apparatus disclosed herein.

As a summary, the current disclosure describes a non-destructive metrology tool which can be used for semiconductor device manufacturing process inspection/monitoring. The metrology tool is well suited for measuring the ONO, OPO stacks for 3D NAND applications using one or more techniques, such as SA-XRD and SAXS. The results have demonstrated high accuracy and precision for up to 72× pair ONO stack and 38× pair OPO stack measurements when checked against SEM/TEM based imaging. The metrology tool 180 is suitable for inspecting CD down to about 10 nm/pair or even about 5 nm/layer which makes the metrology tool suitable for measuring current production ONO or OPO stacks' CD of about 20 nm/layer to about 70 nm/layer. Therefore, metrology tool is well suited for inspection of 3D nano-structures (or 3D super-lattices). The metrology tool may be multi-functional and could also be used for inspection of thin film encapsulation stacks for OLED display applications, such as thin stacks of $A_{l2}O_3/SiO_2$, $Al_2O_3/TiO_2$, or $Al_2O_3/ZrO_2$, and thick stacks of $Al_2O_3$/Polymer, SiN/SiCN, or SiN/pp-HMDSO, etc.

Embodiments of the disclosure have been described above with reference to specific embodiments and numerous specific details are set forth to provide a more thorough understanding of the invention. Persons skilled in the art, however, will understand that various modifications and changes may be made thereto without departing from the broader spirit and scope of the invention. The foregoing description and drawings are, accordingly, to be regarded in an illustrative rather than a restrictive sense.

While the foregoing is directed to the preferred embodiment of the present invention, other and further embodiments of the invention may be devised without departing from the basic scope thereof, and the scope thereof is determined by the claims that follow.

What is claimed is:

1. An apparatus comprising:
a multi-functional X-Ray metrology tool comprising:
a transmitting module having an X-Ray generator and an optic configured for transmitting an incident ray; and
a receiving module having an optic for collecting the incident ray and directing the incident ray to a sensor;
a front end module interfaced with the multi-functional X-Ray metrology tool and controlling automation integration with a multi-chamber system; and
a software module interfaced with the multi-functional X-Ray metrology tool and operable to control the transmitting module and the receiving module, wherein the software module is configured to switch between a first technique comprising at least one of a SAXRD technique and a SAXS technique and a second technique of obtaining X-Ray metrology measurement data comprising at least one or more of grazing incidence X-ray diffraction (GI-XRD), X-ray reflectivity (XRR), high resolution X-ray diffraction (HR-XRD), X-ray fluorescence (XRF), and grazing incidence X-ray fluorescence (GI-XRF) techniques, collect and process the X-Ray metrology measurement data from the sensor.

2. The apparatus of claim 1, further comprising:
a substrate support moveable in at least one direction.

3. The apparatus of claim 2, wherein the substrate support is moveable in an x, y and z direction.

4. The apparatus of claim 1, wherein the transmitting module is configured to transmit the incident ray at an angle of less than 5 degrees from a horizontal and the software module is configurable to collect different data.

5. The apparatus of claim 1, wherein the optic in the transmitting module may be modified to change the incident ray suitable for the first technique to the second technique.

6. The apparatus of claim 1, wherein the software module has a primary and a secondary module, wherein the primary module performs the first technique for capturing and processing data and the secondary module performs the second technique for capturing and processing data.

7. The apparatus of claim 6, wherein the software module further comprises:
an X-Ray metrology Data acquisition, Analysis and Reporting (DAR) module, wherein the DAR module is configured to utilize a physical model for analysis of X-Ray metrology measurement data obtained through the SAXRD technique by the sensor for multilayer measurement for process monitoring in device manufacturing, the physical model using a multi-segmented stack structure to allow for variations of a parameter of layers from different segments, wherein the parameter is at least one of thickness, roughness, and density.

8. The apparatus of claim 7, wherein the software module is configured to detect drift of the parameter of the layers from different segments using the SAXRD data.

9. The apparatus of claim 7, wherein the software module is operable to inspect 3D NAND nano-structure, comprised by various materials, metallic, dielectric, magnetic, crystalline, amorphous, optically opaque, organic and liquid, using the SAXS technique.

10. The apparatus of claim 1, wherein the multi-functional X-Ray metrology tool is configured to inspect:
thin film encapsulation stacks for OLED display applications;
thin stacks of Al2O3/SiO2, Al2O3/TiO2, or Al2O3/ZrO2;
thick stacks of Al2O3/Polymer, SiN/SiCN, or SiN/pp-HMDSO; and
comprising 3D structures.

11. An apparatus comprising:
a multi-chamber system comprising:
a vacuum-tight processing platform, the vacuum-tight processing platform comprising:
a plurality of processing chambers configured to operate below atmospheric pressure, where the plurality of processing chambers may include a transfer chamber having a robot configured to transport a substrate, a chemical vapor deposition chamber, an etch chamber, and a load lock chamber; and
a factory interface having a robot configured to transport the substrate; and
a multi-functional X-Ray metrology tool in communication with the multi-chamber system, the multi-functional X-Ray metrology tool comprising:

a transmitting module having an X-Ray generator and an optic configured for transmitting an incident ray;

a receiving module having an optic for collecting the incident ray and directing the incident ray to a sensor; and a software module interfaced with the multi-functional X-Ray metrology tool and operable to control the transmitting module and the receiving module, wherein the software module is configured to switch between a first technique comprising at least one of a SAXRD technique and a SAXS technique and a second technique of obtaining X-Ray metrology measurement data comprising at least one or more of grazing incidence X-ray diffraction (GI-XRD), X-ray reflectivity (XRR), high resolution X-ray diffraction (HR-XRD), X-ray fluorescence (XRF), and grazing incidence X-ray fluorescence (GI-XRF) techniques, collect and process the X-Ray metrology measurement data from the sensor.

12. The apparatus of claim 11, further comprising:
a substrate support moveable in at least one direction.

13. The apparatus of claim 11, wherein the transmitting module is configured to transmit the incident ray at an angle of less than 3 degrees from a horizontal surface, wherein the angle is configurable to collect different data.

14. The apparatus of claim 11, wherein the optic in the transmitting module may be modified to change the incident ray suitable for the first technique to the second technique.

15. The apparatus of claim 13, wherein the software module has a primary and a secondary module, wherein the primary module is configured to perform the first technique for capturing and processing data and the secondary module is configured to perform the second technique for capturing and processing data.

16. A method of processing a substrate, comprising:
processing a substrate in a chamber having a multi-functional X-Ray metrology tool operationally coupled thereto, the chamber coupled to a multi-chamber system;

obtaining X-Ray metrology measurement data with the multi-functional X-Ray metrology tool in the chamber;

switching with a software module interfaced with the multi-functional X-Ray tool between a first technique comprising at least one of a SAXRD technique and a SAXS technique and a second technique of the obtaining X-Ray metrology measurement data comprising at least one or more of grazing incidence X-ray diffraction (GI-XRD), X-ray reflectivity (XRR), high resolution X-ray diffraction (HR-XRD), X-ray fluorescence (XRF), and grazing incidence X-ray fluorescence (GI-XRF) techniques; and determining a substrate characteristic from the X-Ray metrology measurement data.

17. The method of claim 16, wherein the substrate characteristic includes at least one of critical dimension, etch depth, layer thickness, roughness or density.

18. The method of claim 16, further comprising:
maintaining the chamber and the transfer chamber in a contiguous reduced pressure environment.

19. The method of claim 16, wherein the substrate comprises one of an ONO or OPO stack or other 3D NAND nano-structure.

20. The method of 16, further comprising:
providing a controller in communication with the multi-chamber system and the multi-functional X-Ray metrology tool; and sending instructions from the controller to the multi-chamber system in response to information obtained from the optical measurement to adjust a recipe.

* * * * *